(12) United States Patent
Masuda et al.

(10) Patent No.: US 6,897,326 B2
(45) Date of Patent: May 24, 2005

(54) ASYMMETRICAL BICIPITAL LIPID AND TUBULAR AGGREGATE FORMED BY USING THE SAME

(75) Inventors: Mitsutoshi Masuda, Ibaraki (JP); Toshimi Shimizu, Ibaraki (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/475,700
(22) PCT Filed: Feb. 1, 2002
(86) PCT No.: PCT/JP02/00864
§ 371 (c)(1),
(2), (4) Date: Oct. 20, 2003
(87) PCT Pub. No.: WO02/090370
PCT Pub. Date: Nov. 14, 2002

(65) Prior Publication Data
US 2004/0120998 A1 Jun. 24, 2004

(30) Foreign Application Priority Data
Apr. 26, 2001 (JP) ........................................ 2001-129495

(51) Int. Cl.$^7$ ........................................... C07C 231/00
(52) U.S. Cl. ........................... 554/68; 554/63; 554/209; 424/450
(58) Field of Search ........................... 554/209, 63, 68; 424/450

(56) References Cited

PUBLICATIONS

Toshimi Shimizu & Mitsutoshi Masuda, Journal of The American Chemical Society, 119, 2812 (1997).
Parrot–Lopez Helene et al., Vectorized transport of drugs; synthesis of a new glycosyl derivative of <SYM98>– Cyclodextrin, Tetrahedron Lett., 1992, vol. 33, No. 2, p. 209–212, esp fig. 1 of p. 210.
Parrot–Lopez Helene et al., New β–cyclodextrin derivatives possessing biologically active saccharide antennae, Supramol. Chemical, 1993, vol. 3, No. 1, p. 37–42, esp. fig. 1 of p. 210.
Masuda Mitsutoshi et al., Multilayer structure of an unsymmetrical monolayer lipid mimbrane with a "head–to–tail" interface, Chemical Communication, Dec., 7, 2001, vol. 23, p. 2442–2443.

*Primary Examiner*—Deborah D. Carr
(74) *Attorney, Agent, or Firm*—Gary C Cohn PLLC

(57) ABSTRACT

The present invention is a stable, nanometer scale microtubular aggregated material of an asymmetric double-headed lipid represented by the general formula $$R-NHCO-(CH_2)_n-COOH \qquad (I)$$

(in the formula, R represents an aldopyranose radical from which the terminal reducing hydroxyl group is excluded and n is from six to twenty). The external diameter of the micro-tubular aggregated material is 10–300 nm, and the length is 0.3–10 μm. The micro-tubular aggregated material can be manufactured by dispersing the asymmetric double-headed lipid described above in water at pH of two to eight, next heating to 80–100° C. to dissolve it and then gradually cooling the aqueous solution obtained.

9 Claims, 3 Drawing Sheets

ASYMMETRICAL BICIPITAL LIPID AND TUBULAR AGGREGATE FORMED BY USING THE SAME

TECHNICAL FIELD OF THE INVENTION

The present invention relates to novel lipids and hollow tubular aggregated materials formed from the lipids. More specifically, the present invention relates to an asymmetric double-headed lipid having a sugar at one end and a carboxylic acid at the other end, a micro-tubular aggregated material formed thereof with potential utility as a functional material in the pharmaceutical and cosmetic fields, the electronic data field, the food industry, the agricultural and forestry industry and the fiber industry and a production process therefor.

PRIOR ART

Double-headed peptide lipids to which oligopeptide radicals have been introduced through terminal amide linkages at both ends of long methylene chains are known to be capable of forming stable tubular fiber structures in water (Japanese Patent No. 2,796,613). The solubilities of these lipids, which contain carboxylic acids, can be controlled by the solution pH, and, therefore, these lipids can be dispersed readily in water and controlled easily. However, the system yielded micrometer scale tubes and exhibited problems including difficulty for the system to produce smaller tubes. In contrast, doubled headed glycolipids to which sugar radicals had been introduced through terminal amide linkages on long methylene chains have been known to form extremely fine, stable, helical nanometer scale fibrous structures (Japanese Patent No. 2,692,738, Toshimi Shimizu et. al., Kobunshi Ronbunshu 54, 815 (1997) and Toshimi Shimizu and Mitsutoshi Masuda, Journal of The American Chemical Society, 119, 2812 (1997)). However, the problem with this system was that the solubility of the compound was unconditionally determined limiting the scope of utility.

Problems to be Solved by the Invention

The objectives of the present invention are to offer inexpensive raw materials that can form hollow micro-tubular aggregated materials having potential for use in a broad range of applications and to offer stable nanometer scale micro-tubular aggregated materials that can be formed in water from the raw materials.

Means to Solve the Problems

The inventors conducted an extensive study to solve the aforementioned problem. As a result, the inventors discovered a lipid suited for the purpose upon introducing a long chain fatty acid radical through an amide linkage at the reducing terminal of a glyco radical and discovered that this lipid dispersed well in water and formed a stable, aggregated micro-tubular material.

That is, one objective of the present invention is to present an asymmetric doubled headed lipid represented by a general formula.

R—NHCO—(CH$_2$)$_n$—COOH    (I)

(In the formula, R indicates an aldopyranose radical from which the terminal reducing hydroxyl group is excluded and n is from six to twenty.)

Another objective of the present invention is to present a hollow tubular aggregated material comprising this asymmetric double-headed lipid.

Yet another objective of the present invention is to present a manufacturing process for the tubular aggregated material described above, comprising dispersing the aforementioned asymmetric double-headed lipid in water at a pH of two to eight, heating the dispersion to 80° C. to 100° C. to dissolve the lipid and then gradually cooling the aqueous solution obtained.

EMBODIMENT OF THE INVENTION

In the aforementioned general formula (I) of the present invention, R is an aldopyranose radical from which the terminal reducing hydroxyl group is excluded. That is, R is an aldopyranosyl group wherein the carbon atom at the reducing terminal is involved in an N-glycoside bond. The glucopyranosyl, galactopyranosyl, gulopyranosyl, idopyranosyl and talopyranosyl groups, for example, can be mentioned as such a radical. These tetra-acetyl aldopyranosyl groups may be D isomers, L isomers or racemates, but naturally derived groups are usually in the D form. Furthermore, the reducing terminal carbon atom in an aldopyranosyl group is an asymmetric carbon, and α-anomers and β-anomers may be present. However, either the α-anomer, the β-anomer or a mixture thereof may be used. Those materials in which R is a D-glucopyranosyl group or a D-galactopyranosyl group are particularly ideal since they are easy to manufacture due to the ready availability of the raw materials.

Simultaneously, the alkylene group in the aforementioned general formula (I) is a long chain alkylene group with n being from six to twenty. The hexylene, heptylene, octylene, nonylene, decylene, undecylene, dodecylene, tetradecylene, hexadecylene, octadecylene and icosalene groups and the like, for example, can be mentioned as examples of such an alkylene group.

Asymmetric double-headed lipids represented by the aforementioned general formula (I) are novel compounds not yet found in the literature, but can be readily produced using, for example, the method described here.

A type of azide sugar represented by the general formula

R—N$_3$    (II)

(in the formula, R indicates an aldopyranose radical from which the terminal reducing hydroxyl group is excluded and all of the remaining hydroxyl groups are protected by acetyl groups) is catalytically reduced in methanol in the presence of a platinum oxide catalyst and converted into an amino sugar. Subsequently, a dicarboxylic acid represented by the general formula HOOC—(CH$_2$)$_n$—COOH    (III)

(in the formula, n is an integer six to twenty) is allowed to undergo condensation. Next, the protective acetyl groups on the sugar radicals are removed to produce an asymmetric doubled-headed lipid represented by the general formula (I).

In an azide sugar represented by the aforementioned general formula (II) an azide group is substituted for the terminal reducing hydroxyl group of an aldopyranose and all other hydroxyl groups are entirely acetylated. The azide sugar can be obtained, for example, by using an aldose as the starting material, acetylating all of the hydroxyl groups using anhydrous acetic acid or acetyl chloride, subsequently obtaining an α-brominated sugar having bromine atoms added to the terminal reducing carbon atoms through the action of a solution of hydrogen bromide in acetic acid and sequentially allowing the sugar to react with sodium azide in dimethyl formamide. Since a proton nuclear magnetic resonance spectrum ($^1$H-NMR spectrum in deuterated chloroform at 25° C.) of the obtained product shows a doublet signal (spin-spin coupling constant 8.9 Hz) at 4.65 ppm δ value, it is confirmed that the product is crystalline, air-stable and 100% the β isomer.

Suberic acid, azelaic acid, sebacic acid, 1,9-nonane dicarboxylic acid, 1,14-tetradecane dicarboxylic acid, 1,11-undecane dicarboxylic acid, 1,12-dodecane dicarboxylic acid, 1,13-tridecane dicarboxylic acid, 1,14-tetradecane dicarboxylic acid, 1,16-hexadecane dicarboxylic acid, 1,18-octadecane dicarboxylic acid, and 1,20-eicosane dicarboxylic acid, for example, can be used as the dicarboxylic acid represented by the general formula (III).

In addition to the dicarboxylic acids represented by the general formula (III) described above, monobenzyl carboxylic acid esters represented by the general formula (IV) below containing one terminal carboxylic acid that has been converted to benzyl ester can be used. An azide sugar represented by the general formula $$R-N_3 \qquad (II)$$

(in the formula, R indicates an aldopyranose radical from which the terminal reducing hydroxyl group is excluded and all of the remaining hydroxyl groups are protected by acetyl groups) is catalytically reduced in methanol in the presence of a platinum oxide catalyst and converted into an amino sugar. Subsequently, a dicarboxylic acid monoester represented by the general formula $$HOOC-(CH_2)_n-COOR' \qquad (IV)$$

(in the formula, R' is a radical in a compound containing alcoholic hydroxyl groups, for example, a benzyl group, and n is an integer of from six to twenty) is allowed to undergo condensation [with the amino sugar]. Next, the protective groups are removed by conducting a catalytic hydrogenative decomposition and the sugar radical segment is subsequently de-acetylated to produce an asymmetric double-headed lipid represented by general formula (I).

As the dicarboxylic acid monoesters represented by general formula (IV), the dicarboxylic acids listed as examples above having one carboxylic acid protected by forming an ester using benzyl alcohol, for example, can be mentioned.

Next, a desirable production mode for an asymmetric double-headed lipid of the aforementioned general formula (I) according to the present invention is explained. First, a catalytic reduction of an azide sugar represented by the aforementioned general formula (II) is conducted by, for example, allowing said azide sugar dissolved in methanol to be contacted with hydrogen using platinum oxide as the catalyst to convert it to an amino sugar. At this point, a similar reaction occurs when using a palladium catalyst, but some side reactions occur. Therefore, platinum oxide is favored.

Thin layer chromatography was used to confirm that the azide groups were completely reduced to amino groups, and a condensation of the amino sugar with a dicarboxylic acid represented by the aforementioned general formula (III) without first isolating and purifying the amino sugar formed was conducted. The condensation reaction was performed by blending both reactants in a molar ratio range from equimolar to two equivalents and allowing them to react. N,N-dimethyl formamide, chloroform, methyl alcohol, ethyl alcohol and the like, for example, can be used as the reaction solvent at this point, but N,N-dimethyl formamide (DMF) is ideal among them based on its reactivity and solvent ability. In addition, 1-ethyl-3-(3-dimethyl aminopropyl) carbodiimide hydrochloride, 1-hydroxybenzotriazol, diethyl phosphorocyanidate, 1-ethoxycarbonyl-2-ethoxy-1,2-dihydroquinoline, isobutyl chloroformate and the like which are ordinarily used in peptide syntheses can be used as the condensation agent, but conversions into corresponding reactive derivatives prior to the reaction was ordinarily advantageous. Reactive derivatives customarily used when forming common carboxylic acid amides such as acid halides, acid esters, acid anhydrides, mixed acid anhydrides and the like, for example, can be mentioned. The reaction temperature is selected from a range of −30° C. to 30° C., and the reaction time is ordinarily from 30 minutes to ten hours. The crude reaction products obtained can be purified using, for example, silica gel column chromatography (developing solvent: chloroform/methanol=20/1) to obtain high purity products. The product obtained is dissolved in methanol, and a sodium salt of the desired product having had its sugar radical segment de-acetylated is obtained by allowing a sodium methoxide/methanol solution to act on the methanol solution. Furthermore, a desired carboxylic acid form can be obtained by adding a strongly acidic ion exchange resin to neutralize the sodium salt.

The de-acetylation reaction mentioned above proceeds quantitatively, and purification is not particularly necessary. However, a product of high purity can be obtained upon purification using, for example, silica gel column chromatography when necessary.

An asymmetric double-headed lipid obtained using such a method contains an anomeric carbon in the sugar radical that is 100% the β isomer. This property was confirmed by the $^1$H-NMR spectrum (in deuterated dimethyl sulfoxide at 60° C.) of said asymmetric double-headed lipid having a doubleton (spin-spin coupling constant 8.8 Hz) β value of 4.6 ppm.

The actual elemental analysis results of this compound, for example, agreed with the calculated values within the range of experimental error. Its infrared absorption spectrum exhibited a characteristic absorption band attributed to a sugar hydroxyl group at 3700 cm$^{-1}$ to 3300 cm$^{-1}$, characteristic absorption bands attributed to an oligomethylene chain at 2917 cm$^{-1}$ to 2922 cm$^{-1}$ and 2848 cm$^{-1}$ to 2852 cm$^{-1}$, a characteristic absorption band attributed to carboxylic acid at 1670 cm$^{-1}$ to 1650 cm$^{-1}$, a characteristic absorption band attributed to an amide carbonyl group at 1640 cm$^{-1}$ to 1630 cm$^{-1}$ and a characteristic absorption band attributed to a sugar skeleton at 1100 cm$^{-1}$ to 1000 cm$^{-1}$. Furthermore, signals were observed at δ values of 1.2–1.3 ppm (a methylene hydrogen in a long alkylene chain), 1.4–1.5 ppm (a methylene group hydrogen next to a methylene adjacent to amide groups and carboxyl groups), 2.0 ppm (a methylene group hydrogen adjacent to a carboxyl group), 2.1 ppm (a methylene group hydrogen adjacent to an amide group), 3.0–3.7 ppm (a methene hydrogen in a position other than position 1 in a glucopyranosyl group)

and 4.6 ppm (a methene hydrogen in position 1 of a glucopyranosyl group). Therefore, said compound can be identified as the desired asymmetric double-headed lipid.

Next, when preparing a tubular aggregated material of the present invention, 0.5 mg to 20 mg of an asymmetric double-headed lipid of the present invention is first dispersed in water (1 ml) at a pH of from two to eight, preferably under neutral conditions first, and the dispersion is heated to 80° C. to 100° C. to dissolve it. The aqueous solution obtained is gradually cooled (0.1° C. to 10° C. per minute) and is allowed to stand at room temperature for from one hour to 30 days to obtain a micro-tubular aggregated material in the form of an aqueous dispersion. The shape and size of the aggregated material obtained can be easily confirmed by examining the aggregated material by atomic force microscopy after dropping the solution on a smooth substrate such as a single crystal silicon substrate or a glass substrate.

Micro-tubular aggregated materials having an external diameter of about 10 nm to 300 nm or particularly about 30 nm to 150 nm and a length of 0.3 μm to 10 μm or particularly 0.5 μm to 5 μm can be obtained in the manner described above.

The tubular aggregated materials were thought to be the result of voluntary aggregation without altering the chemical structure of the asymmetric double-headed lipid, and a sheet form obtained through a two-dimensional gathering of the molecules was thought to transform itself into a tube form. However, it is currently unclear whether the tube form is formed by rolling a sheet in the manner cigars are rolled or if it is pipe shaped. The tubular aggregated material is hollow, and the results (FIG. 3) of atomic force microscopic examination of the tubes led the inventors to believe that the ends (that is, both ends) of the tubes are open.

Advantageous Effect of the Invention

According to the present invention, a hollow micro-tubular aggregated material that is stable in water or air can readily be obtained when it was previously difficult to obtain it from common synthetic amphoteric compounds such as natural phospholipids.

The lipids of the present invention, used as the starting material for the micro-tubular aggregated materials, are inexpensive and can also be manufactured easily.

The micro-tubular structured materials of the present invention can be used as gradual release carriers and as adsorbents for medical treatments as well as being useful as emulsifiers, stabilizers, dispersion agents, wetting agents and the like in the cosmetic field, the food industry, agriculture, forestry and the fiber industry. In addition, the material has potential utility in electronic and data fields as nano parts for doping metals and electroconductive substances.

EXAMPLES

The present invention is next explained in further detail using examples, but the present invention is not limited by these examples. The Rf values in thin layer chromatography are reported as $Rf_1$ when a mixed solvent of chloroform/methanol (volumetric ratio 20/1) was used as the development solvent, as $Rf_2$ when a mixed solvent of chloroform/methanol/acetic acid (volumetric ratio 100/3/1) was used as the development solvent and as $Rf_3$ when a mixed solvent of chloroform/methanol/water (volumetric ratio 64/31/5) was used as the development solvent.

Production Example

Five grams (12.2 millimoles) of 2,3,4,6-tetra-O-acetyl-α-D-glucopyranosyl bromide was dissolved in 120 ml of DMF, and 15.8 g (243 millimoles) of sodium azide was added with agitation. The reaction mixture was agitated at room temperature for a day and a night while shielded from light. The reaction mixture was added dropwise to 1,000 ml of ice water with agitation, and the insoluble material was extracted using 900 ml of methylene chloride. The organic phase was washed with ice water and dried using anhydrous sodium sulfate. The drying agent was separated by filtration, and the solvent was completely removed by distillation under reduced pressure. The pale yellow solid obtained was washed using diethyl ether, dried and recrystallized from 2-propanol to obtain 3.30 g (79% yield) of 2,3,4,6-tetra-O-acetyl-β-glucopyranosyl azide in the form of white needle shaped crystals. The physical properties of the product are shown below.

Thin layer chromatography Rf value: $Rf_1 = 0.6$
Melting point: 131° C.–132° C.
Elemental analysis (as $C_{14}H_{19}O_9N_3$)

|  | C | H | N |
|---|---|---|---|
| Calculated values (%) | 45.04 | 5.13 | 11.26 |
| Measured values (%) | 45.36 | 5.10 | 11.14 |

Production Example 2

The same procedure described in Production Example 1 was used with 2,3,4,6-tetra-O-acetyl-α-D-galactopyranosyl bromide used in place of the 2,3,4,6-tetra-O-acetyl-α-D-glucopyranosyl bromide used in Production Example 1 to obtain 3.30 g (79% yield) of 2,3,4,6-tetra-O-acetyl-β-galactopyranosyl azide. The physical properties of the product are shown below.

Thin layer chromatography Rf value: $Rf_1 = 0.7$
Melting point: 96° C.–97° C.
Elemental analysis (as $C_{14}H_{19}O_9N_3$)

|  | C | H | N |
|---|---|---|---|
| Calculated values (%) | 45.04 | 5.13 | 11.26 |
| Measured values (%) | 45.18 | 5.00 | 11.56 |

Production Example 3

One drop of dimethyl formamide and 2.32 ml (32 millimoles) of thionyl chloride were added to 2.29 g (8 millimoles) of 1,14-tetradecane dicarboxylic acid and unreacted thionyl chloride was removed using distillation under reduced pressure after the mixture was heated and refluxed for an hour. 1,14-Tetradecane dicarboxylic acid dichloride was obtained in the form of a pale yellow liquid.

Production Example 4

A method of synthesis for a compound obtained by converting one terminal of 1,14-tetradecane dicarboxylic acid into a benzyl ester is described. The compound can be synthesized by using Japanese Patent Application Public Disclosure (Kokai) Hei 04-18245 or "Organic Synthesis II" pages 276–277 as references. That is, 5 g (17.5 millimoles) of 1,14-tetradecane dicarboxylic acid, 8.37 g of benzyl alcohol, 50 ml of toluene and para-toluene sulfonic acid were placed in a flask and were allowed to reflux while using a Dean Stark dehydration device to remove water. After eight hours of refluxing, about one milliliter of water had been removed. The reaction solution was dissolved in hexane and washed using a saturated sodium bicarbonate solution first and water second. The organic phase was dried using sodium sulfate, and the solvent was removed using reduced pressure distillation. The product was recrystallized using hexane, and 8.1 g of 1,14-tetradecane dicarboxylic acid dibenzyl ester was obtained. Next, 4.8 g (16.7 millimoles) of 1,14-tetradecane dicarboxylic acid, 1.8 g of benzyl alcohol, 50 ml of toluene and sulfuric acid were freshly added to 5.97 g (12.8 millimoles) of this 1,14-tetradecane dicarboxylic acid dibenzyl ester, and the mixture was heated and allowed to reflux for five hours. The reaction mixture was subsequently dissolved in 300 ml of isopropanol/chloroform (1/5 volumetric ratio), and the solution was washed with water and dried using sodium sulfate. The solution was concentrated under reduced pressure and recrystallized using a mixed solvent of ether/hexane (1/4 volumetric ratio) to obtain 3.77 g (10.1 millimoles) of 1,14-tetradecane dicarboxylic acid monobenzyl ester.

Production Example 5

One drop of dimethyl formamide and 2.32 ml of thionyl chloride were added to 3.01 g (8 millimoles) of the 1,14-tetradecane dicarboxylic acid monobenzyl ester obtained in Production Example 4. The reaction mixture was heated and allowed to reflux for one hour. Unreacted thionyl chloride was subsequently removed using distillation under reduced pressure to obtain 3.2 g of 1,14-tetradecane dicarboxylic acid monochloride monobenzyl ester in the form of a pale yellow liquid.

Production Example 6

Eight millimoles (2.98 g) of the 2,3,4,6-tetra-O-acetyl-β-D-glucopyranosyl azide obtained in Production Example 1 was dissolved in 300 ml of methyl alcohol, and 1,000 mg of platinum oxide was added under a nitrogen atmosphere. Next, the reaction mixture was agitated for two hours while introducing hydrogen at room temperature. The reaction mixture was filtered with suction using Celite, and the filtrate was concentrated under reduced pressure. Next, the product was dissolved in 50 ml of DMF containing 0.94 ml of pyridine, and 10 ml of a methylene chloride solution containing 2.59 g (8 millimoles) of the 1,14-tetradecane dicarboxylic acid dichloride obtained in Production Example 3 was added dropwise at 20° C. with agitation. The mixture was returned to room temperature after two hours and was agitated for one day and one night. The reaction mixture was concentrated under reduced pressure and was subsequently extracted using chloroform/water. The organic layer was washed using 5% by weight citric acid, dried using anhydrous sodium sulfate and concentrated under reduced pressure.

The crude product obtained was purified using silica gel column chromatography [elution solution: chloroform/methanol=20/1 (volumetric ratio)], and 1.92 g (39% yield) of a colorless, non-crystalline N-(2,3,4,6-tetra-O-acetyl-β-D-glucopyranosyl) tetradecane-1-carboxamide-14-carboxylic acid was obtained.

| Thin layer chromatography Rf value: $Rf_2 = 0.4$ Elemental analysis (as $C_{30}H_{49}O_{12}N$) | | | |
|---|---|---|---|
| | C | H | N |
| Calculated values (%) | 58.52 | 8.02 | 2.27 |
| Measured values (%) | 58.62 | 8.24 | 2.00 |

Production Example 7

Eight millimoles (2.98 g) of the 2,3,4,6-tetra-O-acetyl-β-D-glucopyranosyl azide obtained in Production Example 1 was dissolved in 300 ml of methyl alcohol, and 1,000 mg of platinum oxide was added under a nitrogen atmosphere. Next, the reaction mixture was agitated for two hours while introducing hydrogen at room temperature. The reaction mixture was filtered with suction using Celite, and the filtrate was concentrated under reduced pressure. Next, the product was dissolved in 50 ml of DMF containing 0.94 ml of pyridine, and 10 ml of a methylene chloride solution containing 2.59 g (8 millimoles) of the 1,14-tetradecane dicarboxylic acid dichloride obtained in Production Example 3 was added dropwise at 20° C. with agitation. The mixture was returned to room temperature after two hours and was agitated for one day and one night. The reaction mixture was concentrated under reduced pressure and was subsequently extracted using chloroform/water. The organic layer was washed using 5% by weight citric acid, dried using anhydrous sodium sulfate and concentrated under reduced pressure.

The crude product obtained was purified using silica gel column chromatography [elution solution: chloroform/methanol=20/1 (volumetric ratio)], and 3.67 g (65% yield) of a colorless, non-crystalline N-(2,3,4,6-tetra-O-acetyl-β-D-glucopyranosyl) tetradecane-1-carboxamide-14-carboxylbenzyl ester was obtained.

| Thin layer chromatography Rf value: $Rf_1 = 0.6$ Elemental analysis (as $C_{37}H_{55}O_{12}N$) | | | |
|---|---|---|---|
| | C | H | N |
| Calculated values (%) | 62.96 | 7.85 | 1.98 |
| Measured values (%) | 62.82 | 7.84 | 2.03 |

One millimole (0.705 g) of the N-(2,3,4,6-tetra-O-acetyl-β-D-glucopyranosyl) tetradecane-1-carboxamide-14-carboxyl benzyl ester obtained was dissolved in methanol, and 100 mg of platinum oxide was added under a nitrogen atmosphere. Next, the reaction mixture was agitated for two hours at room temperature while introducing hydrogen. The reaction mixture was filtered with suction using Celite, and the filtrate was concentration under reduced pressure.

The crude product obtained was purified using silica gel column chromatography [elution solution: chloroform/methanol=20/1 (volumetric ratio)], and 0.610 g (99% yield) of a colorless, non-crystalline N-(2,3,4,6-tetra-O-acetyl-β-D-glucopyranosyl) tetradecane-1-carboxamide-14-carboxylic acid was obtained.

| Thin layer chromatography Rf value: $Rf_2 = 0.4$ Elemental analysis (as $C_{30}H_{49}O_{12}N$) | | | |
|---|---|---|---|
|  | C | H | N |
| Calculated values (%) | 58.52 | 8.02 | 2.27 |
| Measured values (%) | 58.41 | 8.14 | 2.05 |

Production Example 8

Eight millimoles (2.98 g) of the 2,3,4,6-tetra-O-acetyl-β-D-galactopyranosyl azide obtained in Production Example 1 was dissolved in 300 ml of methyl alcohol, and 1,000 mg of platinum oxide was added under a nitrogen atmosphere. Next, the reaction mixture was agitated for two hours while introducing hydrogen at room temperature. The reaction mixture was filtered with suction using Celite, and the filtrate was concentrated under reduced pressure. Next, the product was dissolved in 50 ml of DMF containing 0.94 ml of pyridine, and 10 ml of a methylene chloride solution containing 2.59 g (8 millimoles) of the 1,14-tetradecane dicarboxylic acid dichloride obtained in Production Example 3 was added dropwise at −20° C. with agitation. The mixture was returned to room temperature after two hours and was agitated for one day and one night. The reaction mixture was concentrated under reduced pressure and was subsequently extracted using chloroform/water. The organic layer was washed using 5% by weight citric acid, dried using anhydrous sodium sulfate and concentrated under reduced pressure.

The crude product obtained was purified using silica gel column chromatography [(elution solution: chloroform/methanol=20/1 (volumetric ratio)], and 2.07 g (42% yield) of a colorless, non-crystalline N-(2,3,4,6-tetra-O-acetyl-β-D-galactopyranosyl) tetradecane-1-carboxamide-14-carboxylbenzyl ester was obtained.

| Thin layer chromatography Rf value: $Rf_2 = 0.3$ Elemental analysis (as $C_{30}H_{49}O_{12}N$) | | | |
|---|---|---|---|
|  | C | H | N |
| Calculated values (%) | 58.52 | 8.02 | 2.27 |
| Measured values (%) | 58.80 | 8.16 | 2.10 |

Production Example 9

Eight millimoles (2.98 g) of the 2,3,4,6-tetra-O-acetyl-β-D-galactopyranosyl azide obtained in Production Example 2 was dissolved in 300 ml of methyl alcohol, and 1,000 mg of platinum oxide was added under a nitrogen atmosphere. Next, the reaction mixture was agitated for two hours while introducing hydrogen at room temperature. The reaction mixture was filtered with suction using Celite, and the filtrate was concentrated under reduced pressure. Next, the product was dissolved in 50 ml of DMF containing 0.94 ml of pyridine, and 10 ml of a methylene chloride solution containing 3.16 g (8 millimoles) of the 1,14-tetradecane dicarboxylic acid monochloride monobenzyl ester obtained in Production Example 5 was added dropwise at −20° C. with agitation. The mixture was returned to room temperature after two hours and was agitated for one day and one night. The reaction mixture was concentrated under reduced pressure and was subsequently extracted using chloroform/water. The organic layer was washed using 5% by weight citric acid, dried using anhydrous sodium sulfate and concentrated under reduced pressure.

The crude product obtained was purified using silica gel column chromatography [elution solution: chloroform/methanol=20/1 (volumetric ratio)], and 3.44 g (61% yield) of a colorless, non-crystalline N-(2,3,4,6-tetra-O-acetyl-β-D-glucopyranosyl) tetradecane-1-carboxamide-14-carboxylbenzyl ester was obtained.

| Thin layer chromatography Rf value: $Rf_1 = 0.4$ Elemental analysis (as $C_{37}H_{55}O_{12}N$) | | | |
|---|---|---|---|
|  | C | H | N |
| Calculated values (%) | 62.96 | 7.85 | 1.98 |
| Measured values (%) | 62.15 | 7.64 | 2.13 |

One millimole (0.705 g) of the N-(2,3,4,6-tetra-O-acetyl-β-D-galactopyranosyl) tetradecane-1-carboxamide-14-carboxylbenzyl ester obtained was dissolved in methanol, and 100 mg of platinum oxide was added under a nitrogen atmosphere. Next, the reaction mixture was agitated for two hours at room temperature while introducing hydrogen. The reaction mixture was filtered with suction using Celite, and the filtrate was concentration under reduced pressure.

The crude product obtained was purified using silica gel column chromatography [elution solution: chloroform/methanol=20/1 (volumetric ratio)], and 0.610 g (99% yield) of a colorless, non-crystalline N-(2,3,4,6-tetra-O-acetyl-β-D-galactopyranosyl) tetradecane-1-carboxamide-14-carboxylic acid was obtained.

| Thin layer chromatography Rf value: $Rf_2 = 0.4$ Elemental analysis (as $C_{30}H_{49}O_{12}N$) | | | |
|---|---|---|---|
|  | C | H | N |
| Calculated values (%) | 58.52 | 8.02 | 2.27 |
| Measured values (%) | 58.72 | 7.98 | 2.39 |

Working Example 1

Eighty milligrams (0.136 millimole) of the N-(2,3,4,6-tetra-O-acetyl-β-D-glucopyranosyl) tetradecane-1-carboxamide-14-carboxylic acid obtained in Production Example 6 was dissolved in 3 ml of anhydrous methanol under a nitrogen atmosphere, and 3.53 ml of a 0.05M methanol solution of sodium methoxide was added at room temperature. After agitating the reaction mixture for two hours, the reaction completion was confirmed using thin layer chromatography. About 200 mg of a strongly acidic ion exchange resin (Amberlite IR 120, acid form, and the like) was added to the solution to neutralize the sodium salt, and the target carboxylic acid form composition was obtained.

The composition was purified using silica gel column chromatography [elution solution: chloroform/methanol=

20/1 (volumetric ratio)], and 0.610 g (99% yield) of a colorless, non-crystalline N-(β-D-glucopyranosyl) tetradecane-1-carboxamide-14-carboxylic acid was obtained.

Figure 1:
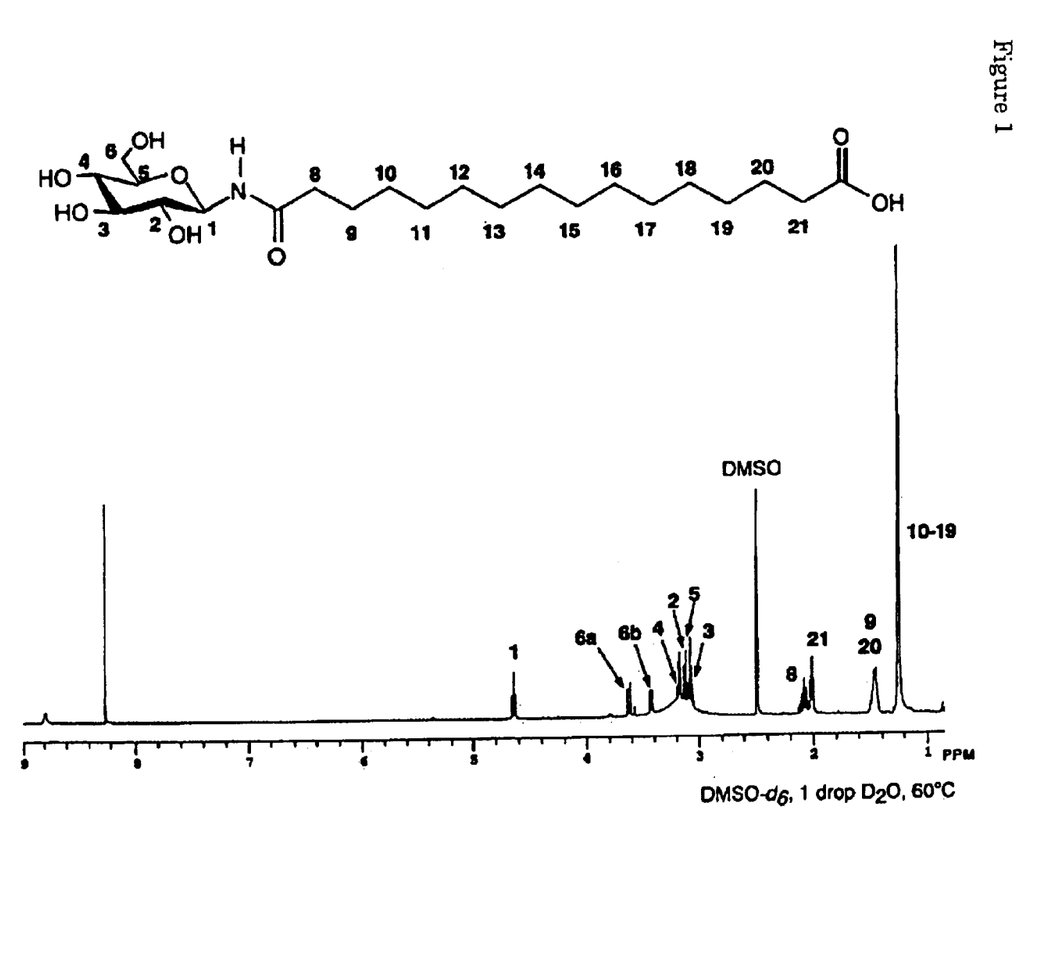
FIG. 1 shows a $^1$H-NMR spectral chart of N-(β-D-glucopyranosyl) tetradecane-1-carboxamide-14-carboxylic acid.

FIG. 1 shows a $^1$H-NMR chart (in deuterated dimethyl sulfoxide at 60° C.) of the compound.

| Thin layer chromatography Rf value: $Rf_3$ = 0.4 Elemental analysis (as $C_{22}H_{41}O_8N_1$) | | | |
|---|---|---|---|
| | C | H | N |
| Calculated values (%) | 59.04 | 9.23 | 3.13 |
| Measured values (%) | 59.00 | 9.02 | 3.30 |

Working Example 2

The same operations used in Working Example 1 were conducted using the N-(2,3,4,6-tetra-O-acetyl-β-D-glucopyranosyl) tetradecane-1-carboxamide-14-carboxylic acid obtained in Production Example 7 in place of the N-(2,3,4,6-tetra-O-acetyl-β-D-glucopyranosyl) tetradecane-1-carboxamide-14-carboxylic acid obtained in Production Example 6, and colorless, non-crystalline N-(β-D-glucopyranosyl) tetradecane-1-carboxamide-14-carboxylic acid was obtained. The analytical results obtained using thin layer chromatography were the same as those obtained in Working Example 1 and are omitted.

Working Example 3

The same operations used in Working Example 1 were conducted using the N-(2,3,4,6-tetra-O-acetyl-β-D-galactopyranosyl) tetradecane-1-carboxamide-14-carboxylic acid obtained in Production Example 8 in place of the N-(2,3,4,6-tetra-O-acetyl-β-D-glucopyranosyl) tetradecane-1-carboxamide-14-carboxylic acid obtained in Production Example 6, and colorless, non-crystalline N-(β-D-galactopyranosyl) tetradecane-1-carboxamide-14-carboxylic acid was obtained.

Figure 2:
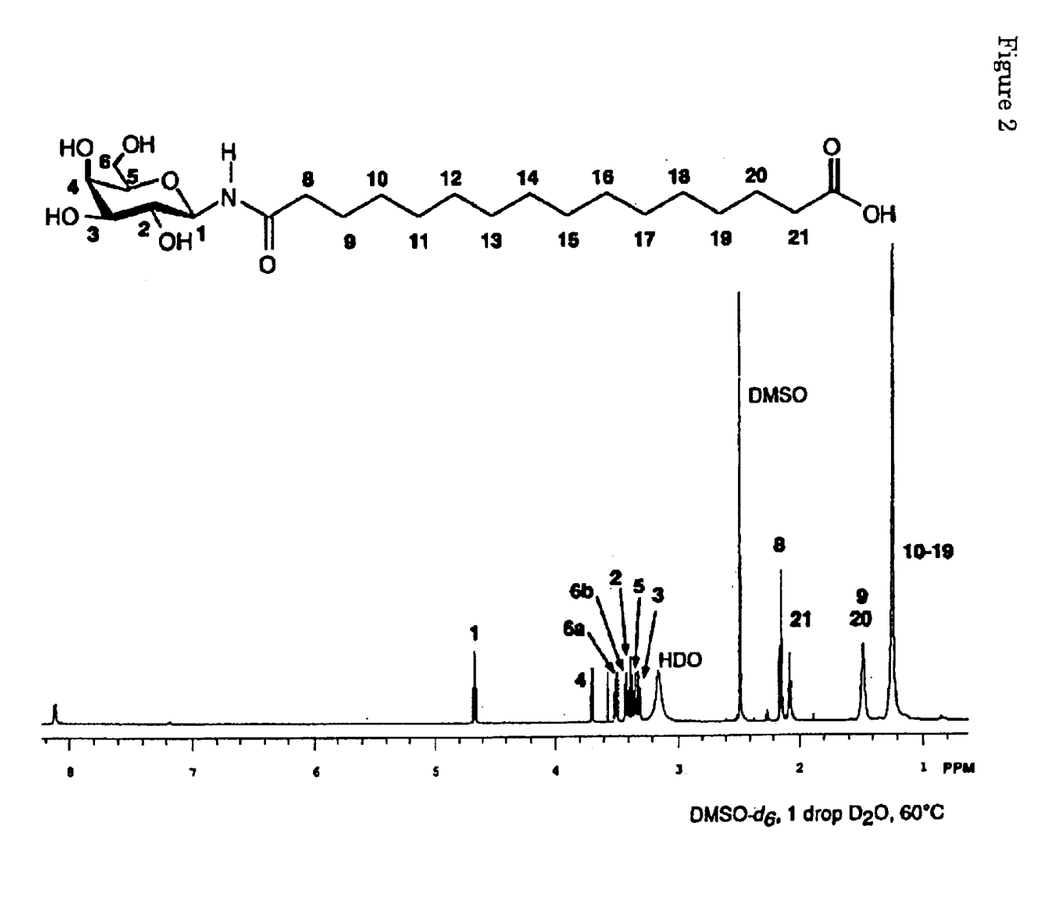
FIG. 2 shows a $^1$H-NMR spectral chart of the N-(β-D-galactopyranosyl) tetradecane-1-carboxamide-14-carboxylbenzyl ester.

A $^1$H-NMR chart (in deuterated dimethyl sulfoxide at 60° C.) of the compound is shown in FIG. 2.

| Thin layer chromatography Rf value: $Rf_3$ = 0.4 Elemental analysis (as $C_{22}H_{41}O_8N_1$) | | | |
|---|---|---|---|
| | C | H | N |
| Calculated values (%) | 59.04 | 9.23 | 3.13 |
| Measured values (%) | 58.93 | 9.45 | 3.03 |

Working Example 4

The same operations used in Working Example 1 were conducted using the N-(2,3,4,6-tetra-O-acetyl-β-D-galactopyranosyl) tetradecane-1-carboxamide-14-carboxylic acid obtained in Production Example 9 in place of the N-(2,3,4,6-tetra-O-acetyl-β-D-glucopyranosyl) tetradecane-1-carboxamide-14-carboxylic acid obtained in Production Example 6, and colorless, non-crystalline N-(β-D-galactopyranosyl) tetradecane-1-carboxamide-14-carboxylic acid was obtained. The analytical results obtained using thin layer chromatography were same as those obtained in Working Example 1 and are omitted.

Working Example 5

Figure 3:
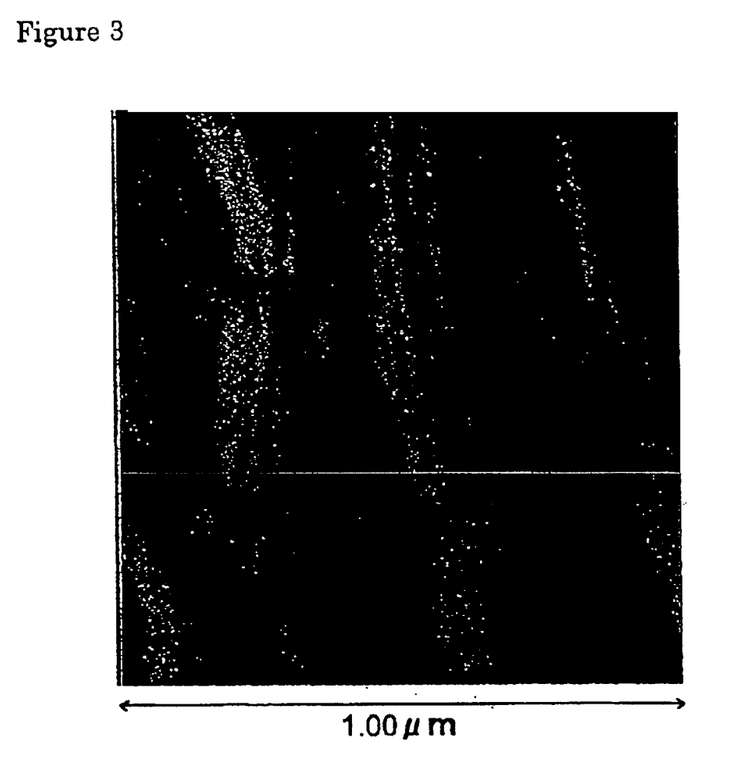
FIG. 3 shows an atomic force microscopy image (after a differential treatment) of the tubular aggregated material obtained in Working Example 5.
Figure 4:
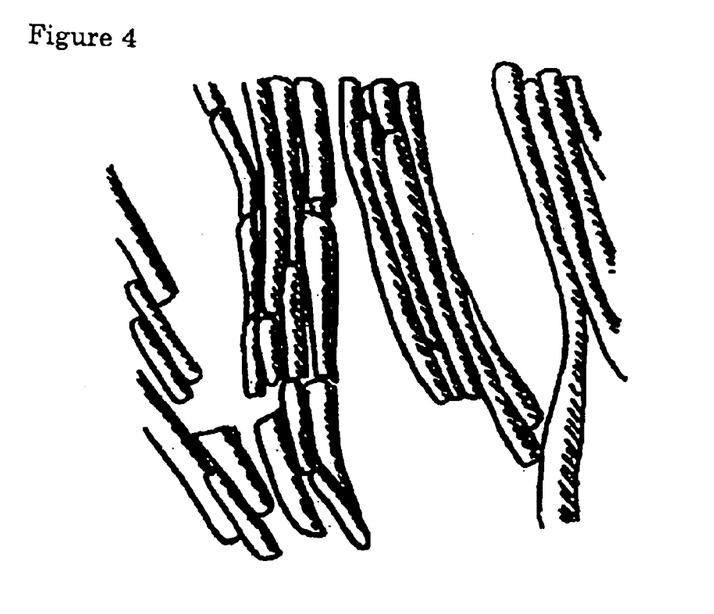
FIG. 4 is obtained by tracing FIG. 3.

Two milligrams of the N-(β-D-glucopyranosyl) tetradecane-1-carboxamide-14-carboxylic acid, the asymmetric double-headed lipid obtained in Working Example 1, were dispersed in water and heated to dissolve (about 95° C.). The solution was gradually cooled (3° C. per minute) to room temperature and was left standing for three days. An aggregated material was obtained in the manner previously described. FIGS. 3 and 4 show photographs taken using a scanning atomic force microscope (Digital Instruments Co., Nanoscope IIIa, deep probe: Single crystal silicon, spring constant: 45N/m, tapping mode, frame size 1 μm). Hollow, tubular shaped aggregated material, 0.5–5 micrometer long, 30–150 nm external diameter and 20–30 nm thick was shown.

Working Examples 6–8

In Working Example 6 hollow, tubular, aggregated materials were obtained using the same operations used in Working Example 5 except that the N-(β-D-glucopyranosyl) tetradecane-1-carboxamide-14-carboxylic acid obtained in Working Example 2 was used. In Working Examples 7 and 8 hollow, tubular, aggregated materials were obtained using the same operations used in Working Example 5, except that the N-(β-D-galactopyranosyl) tetradecane-1-carboxamide-14-carboxylic acids obtained in Working Examples 3 and 4 were used in place of the asymmetric double-headed lipid, N-(β-D-glucopyranosyl) tetradecane-1-carboxamide-14-carboxylic acid, obtained in Working Example 1. The sizes were the same as that in Working Example 5 and are omitted.

What is claimed is:

1. A hollow tubular aggregated material comprising an asymmetric double-headed lipid represented by the general formula $$R\text{---NHCO---}(CH_2)_n\text{---COOH}$$

wherein R represents an aldopyranose radical from which the terminal reducing hydroxyl group is excluded and n is 6–20.

2. A hollow tubular aggregated material as in claim 1, wherein R is D-glucopyranosyl group or a D-galactopyranosyl group.

3. A tubular aggregated material as in claim 1, having an external diameter of 10–300 nm and a length of 0.3–10 μm.

4. A tubular aggregated material as in claim 2, having an external diameter of 10–300 nm and a length of 0.3–10 μm.

5. A process for manufacturing the tubular aggregated material of claim 1, comprising dissolving and heating an asymmetric double-headed lipid represented by the general formula $$R\text{---NHCO---}(CH_2)_n\text{---COOH}$$

wherein R represents an aldopyranose radical from which the terminal reducing hydroxyl group is excluded and n is 6–20, to form a solution in water, and then cooling the solution.

6. The process of claim 5, wherein R is a D-glucopyranosyl group or a D-galactopyranosyl group.

7. The process of claim 5, wherein said asymmetric double-headed lipid is dispersed in water having a pH of 2–8, heated to dissolve the asymmetric double-headed lipid to form a aqueous solution, and the aqueous solution so obtained is gradually cooled.

8. The process of claim 6, wherein said asymmetric double-headed lipid is dispersed in water having a pH of 2–8, heated to dissolve the asymmetric double-headed lipid to form a aqueous solution, and the aqueous solution so obtained is gradually cooled.

9. The process of claim 5, wherein the tubular aggregated material has an external diameter of 10–300 nm and a length of 0.3–10 μm.

* * * * *